(12) United States Patent
Kobayashi et al.

(10) Patent No.: US 7,541,307 B2
(45) Date of Patent: Jun. 2, 2009

(54) METHOD FOR MANUFACTURING AN OPTICALLY ACTIVE HYDROXYMETHYLATED COMPOUND AND A CATALYST THEREFORE

(75) Inventors: Shu Kobayashi, Tokyo (JP); Kei Manabe, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 57 days.

(21) Appl. No.: 11/795,525

(22) PCT Filed: Jan. 27, 2006

(86) PCT No.: PCT/JP2006/301293
§ 371 (c)(1),
(2), (4) Date: Jul. 18, 2007

(87) PCT Pub. No.: WO2006/080425
PCT Pub. Date: Aug. 3, 2006

(65) Prior Publication Data
US 2008/0139835 A1 Jun. 12, 2008

(30) Foreign Application Priority Data
Jan. 31, 2005 (JP) ............... 2005-022643

(51) Int. Cl.
*B01J 31/00* (2006.01)
*C07C 45/00* (2006.01)
*C07C 49/00* (2006.01)

(52) U.S. Cl. .............. 502/167; 556/76; 568/356; 568/395; 568/414

(58) Field of Classification Search ............ 556/76; 502/167; 568/356, 395, 414
See application file for complete search history.

(56) References Cited

FOREIGN PATENT DOCUMENTS

| JP | 2001-252570 | 9/2001 |
|---|---|---|
| JP | 2002-200428 | 7/2002 |

OTHER PUBLICATIONS

Search Report dated Jun. 6, 2006 for International Application No. PCT/JP2006/301293 filed Jan. 27, 2006.
Shu Kobayashi et al., "Bismuth Triflate-Chiral Bipyridine Complexes as Water-Compatible Chiral Lewis Acids," Organic Letters, 2005, pp. 4729-4731, vol. 7, No. 21.
Shunpei Ishikawa et al., "Catalytic Asymmetric Hydroxymethylation of Silicon Enolates Using an Aqueous Solution of Formaldehyde with a Chiral Scandium Complex," Journal of the American Chemical Society, 2004, pp. 12236-12237, vol. 126, No. 39, Easton, PA (USA).
Kei Manabe et al., "Lewis Acid-Catalyzed Asymmetric Hydroxymethylation of Silicon Enolates in Aqueous Media," Tetrahedron, Dec. 22, 2003, pp. 10439-10444, vol. 59, No. 52, Amsterdam, Netherlands.
Yumiko Kaku et al., "A Novel Route for Chiral Synthesis of the Triazole Antifungal ER-30346," Chemical and Pharmaceutical Bulletin, Jul. 1998, pp. 1125-1129, vol. 46, No. 7, Pharmaceutical Society of Japan, Tokyo, Japan.
Chun Wu et al., "Chemical Studies on the Chiral Indanone Derivatives as the Inhibitor ofRenilla Luciferase", Tetrahedron, 2001, pp. 9575-9583, vol. 57, Pergamon Press, Oxford, England.
Rajesh Kumar et al., "Lipase-Catalyzed chemo- and Enantioselective Acetylation of 2-Alkyl/aryl-3-hydroxypropiophenones," Bioorganic & Medicinal Chemistry, 2001, pp. 2643-2652, vol. 9.
Aaron J. Reynolds et al., "The Intramolecular Carboxyarylation Approach to Podophyllotoxin," Journal of the American Chemical Society, Sep. 13, 2003, pp. 12108-12109, vol. 125, American Chemical Society, Easton, PA (USA).
Ryoichi Kuwano et al., "Asymmetric Aldol Reaction of 2-Cyanopropionates Catalysed by Trans-chelating Chiral Diphosphine Ligand TRAP-Rhodium(I) Complex," Chemical Communications, 1998, pp. 71-72, Royal Society of Chemistry, Cambridge, England.
Manabu Wadamoto et al., "Aldol Synthesis with an Aqueous Solution of Formalin," Synlett, 2003, pp. 2219-2221, No. 14.
Jesús Casas et al., "Direct Organocatalytic Asymmetric α-Hydroxymethylation of Ketones and Aldehydes," Tetrahedron Letters, 2004, pp. 6117-6119, No. 45, Pergamon Press, Oxford, England.
Shü Kobayashi, "Lanthanide Trifluoromethanesulfonates as Stable Lewis Acids in Aqueous Media. Yb(OTf)$_3$ Catalyzed Hydroxymethylation Reaction of Silyl Enol Ethers with Commercial Formaldehyde Solution," Chemistry Letters, 1991, pp. 2187-2190.
Makoto Wada et al., "Asymmetric Trimethylsilylcyanation of Aldehydes Utlizing Chiral Bismuth Compounds. A Frontier in Bismuth Mediated Synthetic Reactions," Tetrahedron, 1997, pp. 3939-3946, vol. 8, No. 23, Pergamon Press, Oxford, England.
European Supplementary Search Report corresponding to European Patent Application No. 06712459.4-1211 dated Feb. 4, 2009.

*Primary Examiner*—Porfirio Nazario Gonzalez
(74) *Attorney, Agent, or Firm*—Jenkins, Wilson, Taylor & Hunt, P.A.

(57) ABSTRACT

A silicon enolate represented by the following formula (Formula 1)

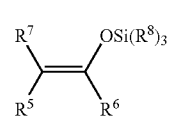

[Chemical Formula 1]

(in the formula, $R^5$ to $R^7$ represent hydrogen atoms, aliphatic hydrocarbon groups, monocyclic or polycyclic alicyclic hydrocarbon groups, monocyclic or polycyclic aromatic or aromatic-aliphatic hydrocarbon groups or heterocyclic groups, $R^5$ and $R^7$ are different, $R^6$ is not a hydrogen atom, each $R^8$ may be identical or different and represents a methyl group, ethyl group or isopropyl group) and formaldehyde are allowed to react in an aqueous solution or a mixed solvent of water and an organic solvent in the presence of a catalyst obtained by mixing a ligand comprising a chiral bipyridine compound or its antipode and Bi(OTf)$_3$.

8 Claims, No Drawings

METHOD FOR MANUFACTURING AN OPTICALLY ACTIVE HYDROXYMETHYLATED COMPOUND AND A CATALYST THEREFORE

CROSS REFERENCE TO RELATED APPLICATIONS

This application is a National Stage of International Application No. PCT/JP2006/301293, filed Jan. 27, 2006, and which claims benefit of Japanese Patent Application No. 2005-022643 filed Jan. 31, 2005, which are incorporated herein in their entirety.

FIELD OF THE INVENTION

This invention relates to an optically active hydroxymethylation reaction. More particularly, this invention relates to a method for manufacturing an optically active hydroxymethylated compound and a catalyst used for the method in a water solvent.

BACKGROUND OF THE INVENTION

Many useful compounds and intermediates thereof containing hydroxymethyl groups on the asymmetric carbon are known. As methods to synthesize these optically active hydroxymethylated compounds, a derivation method (Non-patent Reference 1) using readily available optically active compounds, an optical resolution method (Non-patent References 2 and 3) and a diastereoselective asymmetric synthesis reaction (Non-patent Reference 4) have previously been used. With recent progress in asymmetric synthesis methods, an increasing number of reports about catalytic asymmetric hydroxymethylation reactions have been published. However, problems such as substrate generality, yield, stereoselectivity and the like remain (Non-patent References 5-7, Patent Reference 1).

Formaldehyde, on the other hand, is the most important electrophilic agent used in organic syntheses to increase the number of carbon atoms by one, and methods in which formaldehyde is activated using a Lewis acid are frequently used in hydroxymethylation reactions. However, when a reaction is conducted in an organic solvent formaldehyde needs to be generated from a formaldehyde polymer through thermal decomposition causing serous safety and convenience problems. Formalin, that is, an aqueous solution of formaldehyde, is inexpensive and easy to handle, but formalin is difficult to activate using a Lewis acid since Lewis acids are ordinarily readily hydrolyzed.

The inventors recently discovered that rare earth metal salts are stable in aqueous solutions and function as Lewis acids, and the inventors executed hydroxymethylation reactions in aqueous solutions (Non-patent Reference 8). Furthermore, the inventors recently discovered that a chiral scandium complex was effective in a catalytic asymmetric hydroxymethylation reaction conducted using formalin in an aqueous solution (Non-patent Reference 9).

Similarly, bismuth salts exhibit highly Lewis acid type characteristics and are known to show catalytic activities better than those of scandium depending on reaction type (particularly in reactions conducted in aqueous solutions). In addition, the bismuth cation is almost non-toxic and is less expensive than scandium. However, the cyanolation reaction of aldehydes using trimethylsilyl cyanide in methylene chloride is the only catalytic asymmetric reaction known conducted using a bismuth salt (Non-patent Reference 10).

[Non-patent Reference 1]
Kaku, K. et al., Chem. Pharm. Bull., 46, 1125 (1998).
[Non-patent Reference 2]
Wu, C. et al., Tetrahedron, 57, 9575 (2001)
[Non-patent Reference 3]
Kumar, R. et al., Bioorg. Med. Chem., 9, 2643 (2001)
[Non-patent Reference 4]
Reynolds, A. et al., J. Am. Chem. Soc., 125, 12108 (2003)
[Non-patent Reference 5]
Ito, Y. et al., Chem. Commun., 1998, 71
[Non-patent Reference 6]
Yamamoto, H. et al., Synlett, 2003, 2219
[Non-patent Reference 7]
Cordova, A. et al., Tetrahedron Lett., 45, 6117 (2004)
[Patent Reference 1]
Japanese laid-open application publication (Kokai) No. 2002-200428
[Non-patent Reference 8]
Kobayashi, S. et al., Chem. Lett., 1991, 2187
[Non-patent Reference 9]
Ishikawa, S. et al., J. Am. Chem. Soc., 126, 12236 (2004)
[Non-patent Reference 10]
Wada, M. et al., Tetrahedron: Asymmetry, 8, 3939 (1997)

DISCLOSURE OF THE INVENTION

Problems to be Solved by the Invention

Based on experience, the object of this invention is to present a method to manufacture optically active hydroxymethylated compounds with a broad substrate generality, in high yields and with excellent stereoselectivity when using formaldehyde as the electrophilic agent in aqueous solutions.

Means to Solve the Problems

In order to solve the problems, the inventors investigated the aldol reactions of silicon enolates using formaldehyde, such as formalin and the like, as the electrophilic agent. As a result, the inventors discovered that said reaction proceeded with excellent yield and stereoselectivity when an asymmetric catalyst prepared from a bismuth salt and an optically active bipyridine compound was used. This invention was completed based on the discovery.

That is, this invention is a method for manufacturing an optically active hydroxymethylated compound that allows a silicon enolate represented by the following formula (Formula 1)

[Chemical Formula 1]

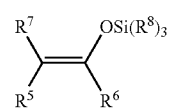

(in the formula, $R^5$ to $R^7$ represent hydrogen atoms, aliphatic hydrocarbon groups, monocyclic or polycyclic alicyclic hydrocarbon groups, monocyclic or polycyclic aromatic or aromatic-aliphatic hydrocarbon groups or heterocyclic groups, $R^5$ and $R^7$ are different, $R^6$ is not a hydrogen atom, each $R^8$ may be identical or different and represents a methyl group, ethyl group or isopropyl group) and formaldehyde to react in an aqueous solution or in a mixed solvent of water and an organic solvent or in a mixed solvent of water and organic solvents in the presence of a catalyst obtained by blending a ligand comprising a chiral bipyridine compound or its antipode and a Lewis acid represented by $BiY_3$ (in the formula, Y represents a halogen atom, OAc, $OCOCF_3$, $ClO_4$, $SbF_6$, $PF_6$ or $OSO_2CF_3$).

Said ligand comprising the chiral bipyridine compound is preferably represented by the following formula (Chemical Formula 2).

[Chemical Formula 2]

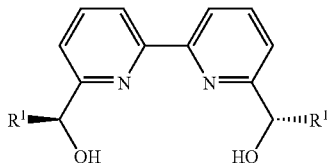

(In the formula, $R^1$ represents an alkyl group containing four or fewer carbon atoms or a phenyl group.)

The molar ratio represented by (said ligand comprising the chiral bipyridine or its antipode/said Lewis acid) is preferably at least 2.5. The addition of 2,2'-bipyridine as an additive is preferred.

In addition, this invention is a catalyst obtained by mixing a ligand comprising a chiral bipyridine compound or its antipode and $Bi(OTf)_3$.

According to this invention, a compound with hydroxymethyl groups bonded to an asymmetric carbon useful, for example, in starting materials or synthetic intermediates for pharmaceutical products, lead compounds and the like can be obtained in high yields and with excellent stereoselectivity in an aqueous solvent by using formaldehyde (for example, formalin) and a bismuth salt as inexpensive and safe starting materials.

BEST MODE FOR CARRYING OUT THE INVENTION

The catalyst used in this invention can be obtained by mixing a ligand comprising a chiral bipyridine compound or its antipode and a Lewis acid represented by $BiY_3$ (in the formula, Y represents a halogen atom, OAc, $OCOCF_3$, $ClO_4$, $SbF_6$, $PF_6$ or $OSO_2CF_3$).

The ligands comprising bipyridine compounds or their antipodes contain two asymmetric carbons bonded to hydroxyl groups and become chiral ligands that control the catalytic activity of a Bi salt in water. The bipyridine compound has a suitable coordination capacity for a Bi salt, does not reduce Lewis acidity and maintains the stereoselectivity of the catalyst without releasing too much cation from the complex comprising the Bi and the ligand.

The use of a bipyridine compound represented by the following formula (Chemical Formula 2) is particularly preferred from the standpoint of Lewis acidity and stereoselectivity.

[Chemical Formula 2]

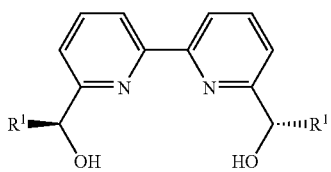

(In the formula, $R^1$ represents an alkyl group containing four or fewer carbon atoms or a phenyl group.)

A Lewis acid represented by $BiY_3$ is used as the bismuth salt. Y represents a halogen atom, OAc, $OCOCF_3$, $ClO_4$, $SbF_6$, $PF_6$ or $OSO_2CF_3$ (OTf). Of these, $Bi(OTf)_3$ is effective. In addition, bismuth cation has an extremely low toxicity and is also less expensive than scandium.

When the ligand is mixed with $BiY_3$ in a solvent, the Bi salt becomes coordinated with the ligand to form a catalyst. As the solvent, aprotic polar solvents that are readily miscible with water, and mixtures of said solvents with water may be listed as examples. As the aprotic polar solvents, ethers such as DME (dimethoxyethane), diglyme (diethylene glycol dimethyl ether) and the like; nitriles such as propionitrile and the like and ketones such as acetone and the like may be cited. These organic solvents may be mixed in a proportion of 1 to 19 (volume ratio) per one of water.

The individual concentrations of the ligands and $BiY_3$, such as $Bi(OTf)_3$ and the like, of about 0.01 to 0.1 moles/liter in a solvent is preferred.

In this invention, this catalyst is used in an asymmetric hydroxymethylation reaction (Chemical Equation 3) of formaldehyde and the silicon enolates described below.

[Chemical Equation 3]

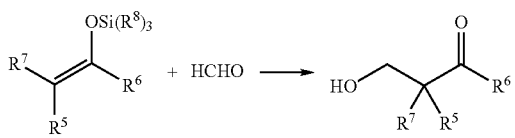

$R^5$ to $R^7$ represent hydrogen atoms, aliphatic hydrocarbon groups, monocyclic or polycyclic alicyclic hydrocarbon groups, monocyclic or polycyclic aromatic or aromatic-aliphatic hydrocarbon groups or heterocyclic groups, and they may also contain substituents. As the hydrocarbon groups or heterocyclic groups, alkyl groups such as methyl, ethyl, propyl, isopropyl, butyl and the like, cyclohexyl groups, phenyl groups, phenyl ethyl groups, phenyl vinyl groups, naphthyl groups, furyl groups, thienyl groups and the like, for example, may be listed as examples. In addition, the substituents that also may be present may be halogen atoms, alkoxy groups, thioalkoxy groups, hydrocarbon groups and the like.

$R^5$ to $R^7$ are preferably as listed below.

$R^5$ represents a hydrogen atom or an alkyl group, $R^6$ represents an alkyl group, alkyl aryl group, aryl group or sulfide group. However, a section of $R^5$ and $R^6$ may together form a five to six membered ring comprising carbon and optional hetero atoms or preferably carbon atoms part of which may form an aromatic ring. $R^7$ represents a hydrogen atom, an alkyl group, an alkyl aryl group or an aryl group.

In addition, $R^5$ and $R^7$ are different.

Each $R^8$ represents a hydrocarbon group. These may be identical or different, but identical groups are preferred. $R^8$ is a methyl group, ethyl group or isopropyl group.

The reaction is allowed to occur in an aqueous solution or a mixed solvent of water and an organic solvent. At this point, the organic solvent used in the form of a mixed solvent with water may be dimethoxyethane (DME), tetrahydrofuran (THF), acetonitrile, dioxane and the like that easily blend with water, but DME, THF, acetonitrile and dioxane can be listed as preferred examples. The mix ratio for the organic solvent and water is not particularly restricted, but the mixed solvent generally contains at least 1% by weight and more preferably at least 5% by weight of water.

The amount of the aqueous solution or the mixed solvent used may be appropriately selected. Ordinarily, however, a proportion of two to fifty weight fold is considered, for example, as the amount needed to dissolve the starting material substances and the catalyst.

The HCHO/silicon enolate molar ratio in a reaction solution is preferably one to fifty and more preferably about one to ten. In addition, the catalyst is used at 1 to 50 mole % of the silicon enolate and is more preferably used at 5 to 20 mole %.

The reaction temperature is −30° C. to ambient temperature, and a more ideal range is −15 to 0° C.

The reaction time may be decided appropriately, and 0.5 to 50 hours, for example, may be used.

An optically active hydroxymethylated compound is formed using this reaction.

In the method of this invention, a molar ratio of at least 2.5 is preferred and at least three is more preferred for the (said ligand comprising the chiral bipyridine compound or its antipode/said Lewis acid). When said molar ratio is less than 2.5, the product yield and selectivity tend to decline. The most preferred range for said molar ratio is three to four.

Moreover, the addition of 2,2'-bipyridine as an additive is preferred in the method of this invention. When the reaction described above is allowed to occur upon adding 2,2'bipyridine, the amount of the catalyst added can be reduced without adversely affecting the yield and the selectivity. As the amount of 2,2'-bipyridine added, at least five moles per mole of said bismuth salt, for example, is preferred. When the amount of 2,2'-bipyridine added is three moles or less, the product yield tends not to improve sufficiently. In addition, when the amount added exceeds five moles, the effect becomes saturated.

The present invention is illustrated in the following examples, but these examples are not intended to limit the scope of the present invention.

EXAMPLE 1

A chiral bipyridine with the structure of the following formula (Chemical Formula 2) was prepared according to the method described in Non-patent Reference 3.

[Chemical Formula 2]

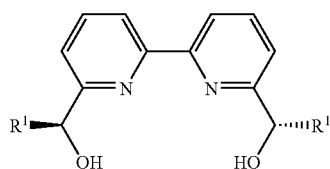

DME (0.50 ml) was added to a metal salt, $MX_n$ (0.020 mmole of the compounds listed in Table 1 below), that had been dried for an hour at 200° C. under vacuum. The ligand 1a described above [$R^1$=tert-Bu, 0.022 mmole in a compound of the formula above (Chemical Formula 2)] was added to this solution, and the mixture was agitated at room temperature until the mixture was clear. The temperature of the solution was lowered to 0° C., and an aqueous HCHO solution (35%, 86 mg, 1.0 mmole) and silicon enolate 2 [a compound (0.20 mmole) of the following chemical formula (Chemical Formula 4)] was added. A saturated aqueous sodium bicarbonate solution was added after four hours of agitation, and three $CH_2Cl_2$ extractions of the aqueous layer were performed. The organic layer was dried using $Na_2SO_4$, the solvent was removed by distillation under reduced pressure and the residue was purified using silica gel thin layer chromatography (hexane:AcOEt=2:1). The volume ratio of water/DME was 1/9.

[Chemical Formula 4]

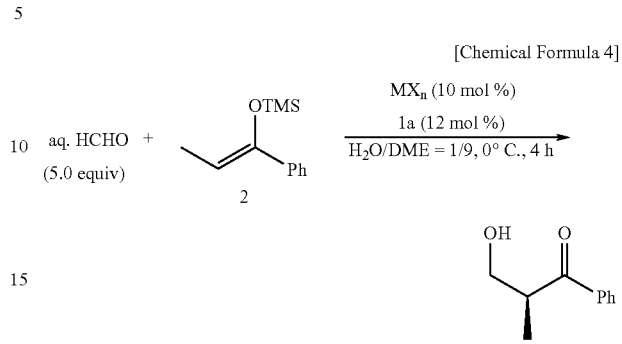

The results obtained are shown in Table 1. In the table, the term "trace" signifies that a substance was almost not detected. In addition, Ee indicates the enantiomer excess ratio.

TABLE 1

| Experimental Examples | $MX_n$ | Yield (%) | Ee(%) |
|---|---|---|---|
| 1 | Fe(OTf)$_3$ | 25 | 20 |
| 2 | Cu(OTf)$_2$ | 8 | −58 |
| 3 | AgOTf | trace | 53 |
| 4 | Cd(ClO$_4$)$_2$ | 4 | 0 |
| 5 | Yb(OTf)$_3$ | 4 | 32 |
| 6 | Zn(OTf)$_2$ | 8 | 0 |
| 7 | Pb(OTf)$_3$ | 10 | 10 |
| 8 | Ga(OTf)$_3$ | 3 | 0 |
| 9 | Sb(OTf)$_3$ | trace | 18 |
| 10 | In(OTf)$_3$ | 10 | 64 |
| 11 | Sc(OTf)$_3$ | 70 | 84 |
| 12 | Bi(OTf)$_3$ | 78 | 92 |
| 13 | BiF$_3$ | 0 | — |
| 14 | BiCl$_3$ | trace | 0 |
| 15 | BiBr$_3$ | trace | 2 |
| 16 | BiI$_3$ | 5 | 16 |

The results reported in Table 1 indicate that the product yields were high and Ee was also high when scandium triflate and bismuth triflate were used (Experimental Examples 11 and 12).

EXAMPLE 2

Exactly the same procedure described in Example 1 was used with the exception that Bismuth triflate, 3 mole %, was used as the metal salt, and 9 mole % of the ligand 1a was used and furthermore the solvents indicated in Table 2 were used in place of DME.

[Chemical Reaction 5]

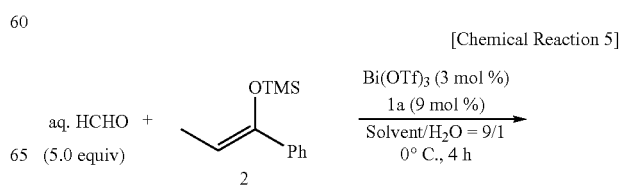

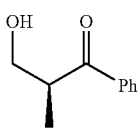

The results obtained are reported in Table 2. The symbols used in the table had the same significance described in Table 1.

TABLE 2

| Experimental Examples | Solvent | Yield (%) | Ee(%) |
|---|---|---|---|
| 17 | DME | 67 | 92 |
| 18 | THF | 32 | 80 |
| 19 | EtOH | trace | 85 |
| 20 | H$_2$O | 7 | 46 |
| 21 | DMF | 5 | 46 |
| 22 | Propionitrile | 51 | 85 |
| 23 | Ethylene glycol | trace | −8 |
| 24 | Diglyme | 58 | 89 |
| 25 | Acetone | 74 | 90 |

According to the results reported in Table 2, the product yield was high and Ee was also high when DME (dimethoxyethane, Experimental Example 17), propionitrile (Experimental Example 22), diglyme (Experimental Example 24) and acetone (Experimental Example 25) were used.

EXAMPLE 3

Exactly the same procedure described in Example 1 was used with the exception that the amounts of bismuth triflate and ligand 1a were changed and, in addition, the reaction temperature was changed. However, the silicon enolate concentration was 0.36 M.

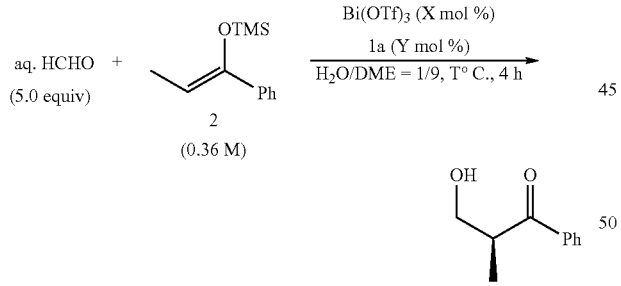

[Chemical Equation 6]

The results obtained are reported in Table 3. The symbols used in the table have the same significance as described in Table 1. Now, the amount of bismuth triflate was X% by mole, the amount of ligand 1a was Y% by mole and the reaction temperature was T° C. as shown in the table.

TABLE 3

| Experimental Example | X | Y | T | Yield (%) | Ee(%) |
|---|---|---|---|---|---|
| 26 | 10 | 30 | 0 | 92 | 93 |
| 27 | 5 | 15 | 0 | 81 | 92 |
| 28 | 3 | 9 | 0 | 67 | 92 |
| 29 | 3 | 9 | 10 | 76 | 92 |
| 30 | 1 | 3 | 0 | 63 | 92 |
| 31[a] | 1 | 3 | 0 | 73 | 92 |

[a] [Silicon enolate] = 0.72 M

According to the results reported in Table 3, the stereoselectivity was good in all of Experimental Examples 26 to 31 even when the conditions were changed. In addition, the yield improved in Experimental Example 29 compared to Experimental Example 28 when the reaction temperature was raised. In addition, the yield improved in Experimental Example 26 compared to Experimental Example 27 when the substrate concentration was raised.

EXAMPLE 4

Exactly the same procedure described in Example 1 was used with the exception that the amount of ligand 1a in relation to bismuth triflate was changed.

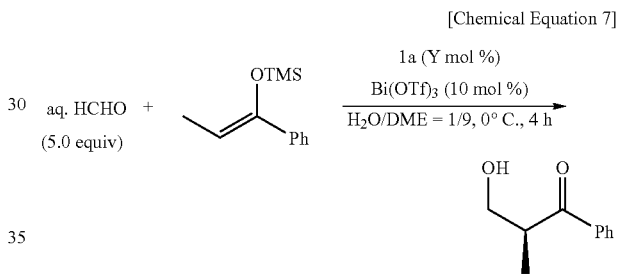

[Chemical Equation 7]

Now, the chemical formula of ligand 1a in all of the examples is represented by Chemical Formula 8.

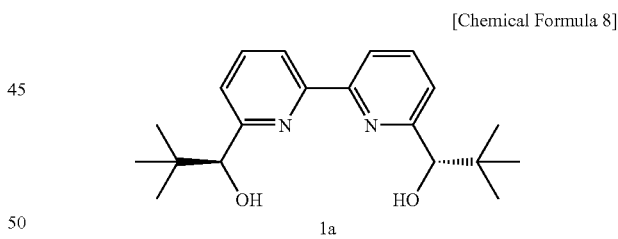

[Chemical Formula 8]

The results obtained are reported in Table 4. The symbols used in the table have the same significance as described in Table 1. Now, the amount of bismuth triflate was 10 mole % in the table, and the amount of ligand 1a is represented as Y mole %.

TABLE 4

| Experimental Example | Y | Yield (%) | Ee(%) |
|---|---|---|---|
| 32 | 5 | 6 | 44 |
| 33 | 10 | 18 | 71 |
| 34 | 12 | 26 | 78 |
| 35 | 15 | 33 | 80 |
| 36 | 20 | 36 | 84 |

TABLE 4-continued

| Experimental Example | Y | Yield (%) | Ee(%) |
|---|---|---|---|
| 37 | 24 | 72 | 91 |
| 38 | 30 | 92 | 93 |
| 39 | 40 | 84 | 91 |

According to the results reported in Table 4, the yield and Ee were high in Experimental Examples 37 to 39 when the molar ratio, [ligand 1a (mole %)/bismuth triflate (mole %)], was at least 2.4. The highest yield and Ee were observed in Experimental Example 38 when the ratio described above was three.

EXAMPLE 5

Furthermore, exactly the same procedure described in Example 1 was used with the exception that a five fold molar ratio of 2,2'-bipyridine to the bismuth salt was added as an additive and the proportions of bismuth triflate and ligand 1a and the reaction time were changed (Experimental Examples 43 and 44).

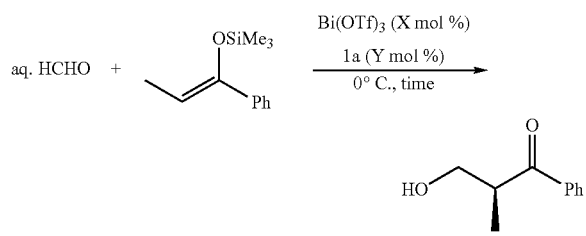

[Chemical Equation 9]

The results obtained are reported in Table 5. The symbols used in the table have the same significance as described in Table 1. Now, the amount of bismuth triflate was represented by X mole % in the table, and the amount of ligand 1a was represented as Y mole %.

TABLE 5

| Experimental Example | solvent | x | y | time (h) | yield[a] (%) | ee[b] (%) |
|---|---|---|---|---|---|---|
| 40 | H$_2$O/DME = 1/9 | 10 | 30 | 4 | 92 | 93 |
| 41 | H$_2$O/DME = 1/9 | 3 | 9 | 4 | 67 | 92 |
| 42 | H$_2$O/DME = 1/9 | 1 | 3 | 4 | 63 | 83 |
| 43[a] | H$_2$O/DME = 1/9 | 1 | 3 | 21 | 93 | 91 |
| 44[b] | H$_2$O/DME = 1/9 | 0.5 | 1.5 | 16 | 76 | 90 |

[a] 5 mol % of 2,2'-bipyridine was added.
[b] 2.5 mol % of 2,2'-bipyridine was added.

Now, Experimental Examples 40, 41 and 42 were identical to Experimental Examples 26, 28 and 30, respectively.

According to the results reported in Table 5, the yield and Ee both declined when the amount of catalyst used was decreased (Experimental Examples 40 to 42). In Experimental Example 42, silicon enolate, one of the substrates, disappeared four hours after the reaction started and the reaction stopped (yield 63%). In contrast, the reaction proceeded while silicon enolate still remained twenty-one hours after the reaction started, the yield improved significantly and Ee also rose in Experimental Example 43 when 2,2'-bipyridine was also added, although the values of x and y were identical to those of Experimental Example 42. The yield decreased slightly, but the selectivity was maintained in Experimental Example 44 when the amount of catalyst (represented by x in the table) was further decreased to 0.5 mole %.

EXAMPLE 6

A reaction was allowed to occur using exactly the same procedure as that of Example 1 with the exception that various substrates were used and 2,2'-bipyridine was added as an additive based on the results reported above. However, the amount of bismuth triflate used was 1 mole %, the amount of ligand 1a was 3 mole %, the amount of 2,2'-bipyridine was 5 mole %, and the solvent had a water/DME volume ratio of 1/4. In addition, the reaction time was changed according to the substrates.

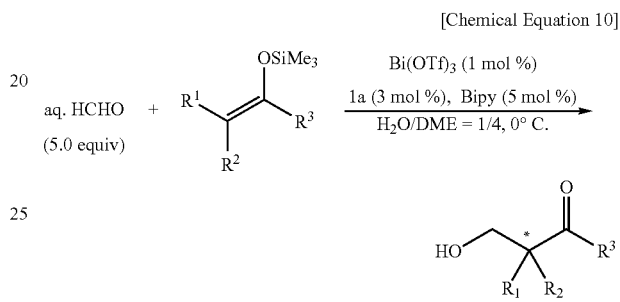

[Chemical Equation 10]

The results obtained are shown in Tables 6 and 7. The symbols in the table have the same significance described in Table 1.

TABLE 6

| Experimental Example | silicon enolate | time (h) | yield (%) | ee (%) |
|---|---|---|---|---|
| 45 | OSiMe$_3$, R=Me, Ph | 21 | 93 | 91 |
| 46 | R=Et | 70 | 79 | 92 |
| 47 | OSiMe$_3$, X=MeO | 30 | 80 | 88 |
| 48 | X=Cl | 34 | 87 | 89 |
| 49 | OSiMe$_3$, naphthyl-OMe | 22 | 59 | 92 |
| 50 | Me$_3$SiO-indene | 9 | 89 | 88 |

TABLE 7

| Experimental Example | silicon enolate | time (h) | yield (%) | ee (%) |
|---|---|---|---|---|
| 51 | OSiMe₃, R = Me | 22 | 81 | 95 |
| 52 | R = C₄H₉ | 22 | 68 | 93 |
| 53 | OSiMe₃ (methylcyclohexenyl) | 20 | 66 | 77 |
| 54 | OSiMe₃ (PhCH₂-cyclohexenyl) | 48 | 79 | 92 |
| 55 | OSiMe₃ (Ph-cyclohexenyl) | 20 | 82 | 79 |

Based on the results reported in Tables 6 and 7, this asymmetric reaction system was demonstrated to be effective with various substrates.

What is claimed is:

1. A method for manufacturing an optically active hydroxymethylated compound that allows a silicon enolate represented by the following formula (Formula 1)

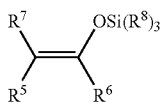

(in the formula, $R^5$ to $R^7$ represent hydrogen atoms, aliphatic hydrocarbon groups, monocyclic or polycyclic alicyclic hydrocarbon groups, monocyclic or polycyclic aromatic or aromatic-aliphatic hydrocarbon groups or heterocyclic groups, $R^5$ and $R^7$ are different, $R^6$ is not a hydrogen atom, each $R^8$ may be identical or different and represents a methyl group, ethyl group or isopropyl group) and formaldehyde to react in an aqueous solution or in a mixed solvent of water and an organic solvent or in a mixed solvent of water and organic solvents in the presence of a catalyst obtained by blending a ligand comprising a chiral bipyridine compound or its antipode and a Lewis acid represented by $BiY_3$ (in the formula, Y represents a halogen atom, OAc, $OCOCF_3$, $ClO_4$, $SbF_6$, $PF_6$ or $OSO_2CF_3$).

2. A method described in claim 1 wherein said ligand comprising the chiral bipyridine compound is represented by the following formula (Chemical Formula 2)

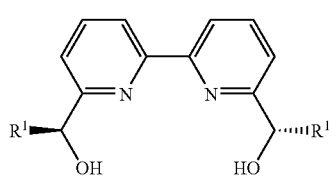

(in the formula $R^1$ represents an alkyl group with four or fewer carbon atoms or a phenyl group).

3. The method described in claim 1 wherein the molar ratio represented by (said ligand comprising the chiral bipyridine compound or its antipode/said Lewis acid) is at least 2.5.

4. A catalyst obtained by mixing a ligand comprising a chiral bipyridine compound or its antipode and $Bi(OTf)_3$.

5. The method described in claim 2, wherein the molar ratio represented by (said ligand comprising the chiral bipyridine compound or its antipode/said Lewis acid) is at least 2.5.

6. The method described in claim 1, wherein a 2,2'-bipyridine is also added as an additive.

7. The method described in claim 2, wherein a 2,2'-bipyridine is also added as an additive.

8. The method described in claim 3, wherein a 2,2'-bipyridine is also added as an additive.

* * * * *